United States Patent
Drake

(10) Patent No.: US 11,331,453 B1
(45) Date of Patent: May 17, 2022

(54) FOLEY CATHETER STABILIZING APPARATUS

(71) Applicant: Michelle Lynn Drake, Vancouver, WA (US)

(72) Inventor: Michelle Lynn Drake, Vancouver, WA (US)

( * ) Notice: Subject to any disclaimer, the term of this patent is extended or adjusted under 35 U.S.C. 154(b) by 0 days.

(21) Appl. No.: 17/471,528

(22) Filed: Sep. 10, 2021

(51) Int. Cl.
*A61M 5/32* (2006.01)
*A61M 25/02* (2006.01)
*A61M 25/00* (2006.01)

(52) U.S. Cl.
CPC ........ *A61M 25/02* (2013.01); *A61M 25/0017* (2013.01); *A61M 2025/026* (2013.01); *A61M 2025/0213* (2013.01); *A61M 2210/086* (2013.01); *A61M 2210/1085* (2013.01)

(58) Field of Classification Search
CPC .......... A61M 25/02; A61M 2025/0206; A61M 2025/0253; A61M 2025/0213; A61M 2025/026; A61M 2210/1085
See application file for complete search history.

(56) References Cited

U.S. PATENT DOCUMENTS

| | | | | |
|---|---|---|---|---|
| 4,416,664 A | | 11/1983 | Womack | |
| 4,617,017 A | * | 10/1986 | Hubbard | A61M 25/02 128/DIG. 26 |
| 5,690,617 A | * | 11/1997 | Wright | A61M 25/02 128/DIG. 26 |
| 6,296,164 B1 | * | 10/2001 | Russo | A61F 5/449 224/581 |
| 6,582,403 B1 | | 6/2003 | Bierman | |
| 9,358,368 B2 | | 6/2016 | Beran | |
| 9,480,821 B2 | * | 11/2016 | Ciccone | A61M 25/0017 |
| 2005/0273058 A1 | | 12/2005 | Bierman | |
| 2006/0058738 A1 | | 3/2006 | Ponzi | |
| 2006/0135944 A1 | | 6/2006 | Bierman | |
| 2009/0182283 A1 | * | 7/2009 | Sloan | A61M 25/02 604/180 |
| 2017/0043072 A1 | * | 2/2017 | Vigil | A61M 1/062 |
| 2018/0154117 A1 | * | 6/2018 | Roberts | A61M 25/02 |

* cited by examiner

*Primary Examiner* — Rebecca E Eisenberg

(57) ABSTRACT

A foley catheter stabilizing apparatus includes an attachment strap, a mounting plate, and a catheter stabilizing retainer. The catheter stabilizing retainer that secures the port divider of the catheter includes a channeled holder, an elastic cover, and a male fastening feature. The attachment strap slidably traverses through the mounting plate. A base of the channeled holder is rotatably mounted to the mounting plate as the attachment strap secures the mounting plate and the catheter stabilizing retainer to patient's leg. A proximal end of the elastic cover is terminally connected to a first lateral wall of the channeled holder. The male fastening feature is angularly connected to a second lateral wall of the channeled holder. The elastic cover is stretched across the first lateral wall and the second lateral wall of the channeled holder and removably mounted to the male fastening feature to secure the port divider in place.

7 Claims, 9 Drawing Sheets

FOLEY CATHETER STABILIZING APPARATUS

FIELD OF THE INVENTION

The present invention relates generally to a foley catheter attachment. More specifically, the present invention provides a foley catheter stabilizing apparatus that enables the port divider of the foley catheter to mount with the left side orientation or the right side orientation.

BACKGROUND OF THE INVENTION

A foley catheter is a thin, sterile tube inserted into the bladder to drain urine. Because it can be left in place in the bladder for a period of time, it is also called an indwelling catheter. Foley catheter is held in place with a balloon at the tip end of the catheter, which is filled with sterile water to prevent the catheter from being removed from the bladder. The urine drains through the catheter into a bag, which is emptied when full. Existing catheter stabilization devices that swivel are placed on the patients' skin with adhesive and are stuck in the same place until changed and require daily maintenance and need changing typically every 7 to 10 days. These existing catheter stabilization devices have issues with lift (where part of the adhesive loses stick), pain at removal, and skin conditions under the adhesive; leading to skin breakdown and pressure ulcers. Furthermore, a retainer of the existing catheter stabilization device that secures the port divider of the catheter tends to break down or not close properly due to the ridged structural configuration thus compromising the functionality. Furthermore, existing retainers are configured in two different channels to receive the port divider so that the drainage port and the balloon port of the catheter have to be placed within specific channels. The two different channels can accidently lead into incorrect placement of the port divider thus compromising the functionality of the foley catheter.

It is therefore an objective of the present invention provide a foley catheter stabilizing apparatus that overcomes the aforementioned problems. More specifically, the present invention completely eliminates skin breakdown by replacing the adhesive element of the existing catheter with a leg band. The retainer of the present invention configured with an elastic cap to improve reliability and to simplify fastening and unfastening of the elastic cap for the patients with hand dexterity and mobility issues. The retainer of the present invention is sized to fit both the drainage port and the balloon port of the catheter so that the port divider can secured with any orientation.

DETAIL DESCRIPTIONS OF THE INVENTION

All illustrations of the drawings are for the purpose of describing selected versions of the present invention and are not intended to limit the scope of the present invention.

The present invention is a foley catheter stabilizing apparatus that secures a foley catheter in place, reducing the risk of urethral erosion, bladder spasms, and trauma. The present invention is attached to a leg band in order to eliminate compromising the integrity of the patients' skin with adhesive material avoiding pain, skin break down, and pressure ulcers. The present invention is a medical device that allows ambidextral positioning of a port divider of the catheter, continuous reuse, and is user friendly for those with or without hand dexterity and mobility issues.

Figure 1:
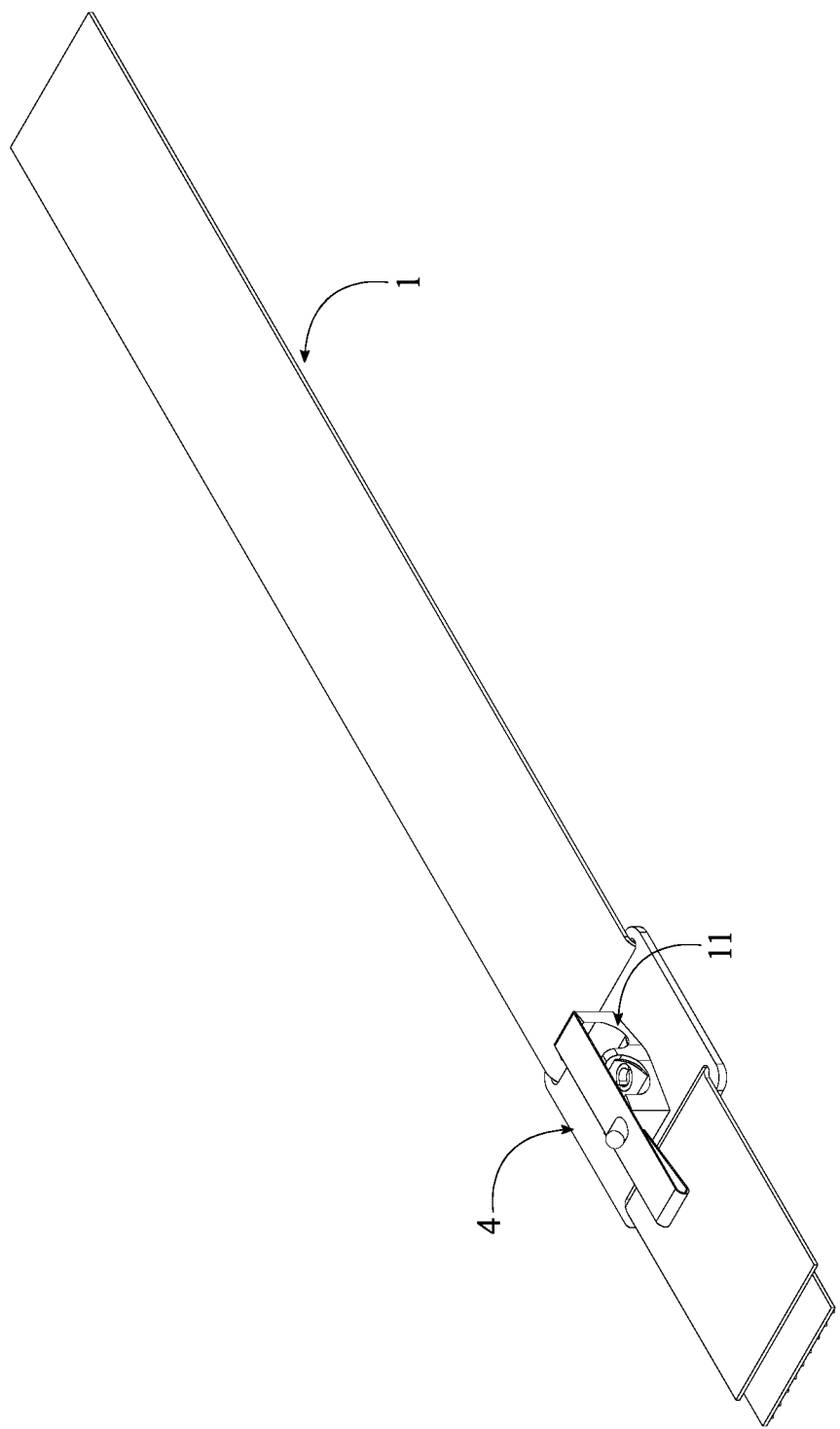
FIG. 1 is a top perspective view of the present invention, wherein the catheter stabilizing retainer is in the closed position.
Figure 2:
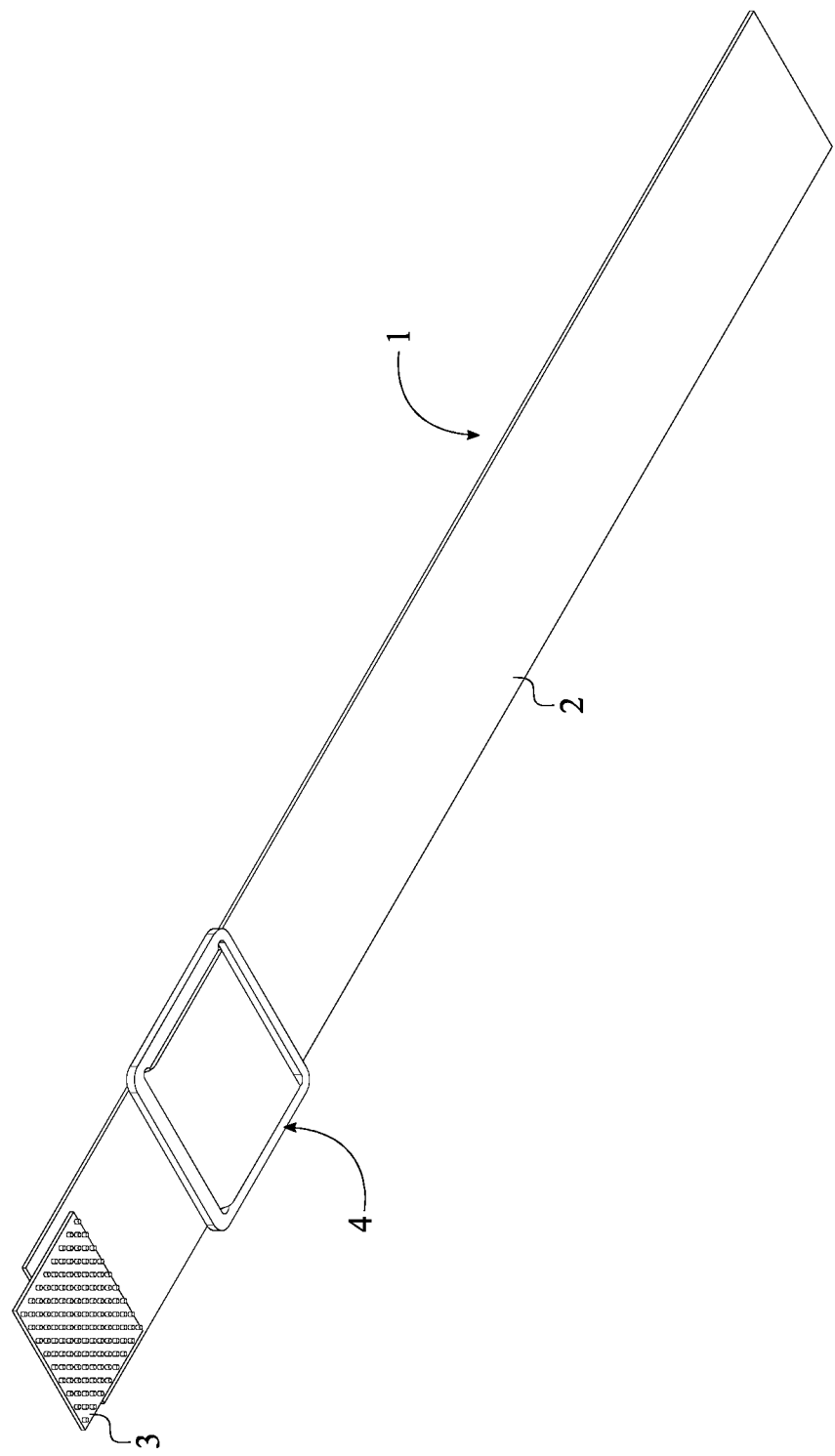
FIG. 2 is a bottom perspective view of the present invention.
Figure 3:
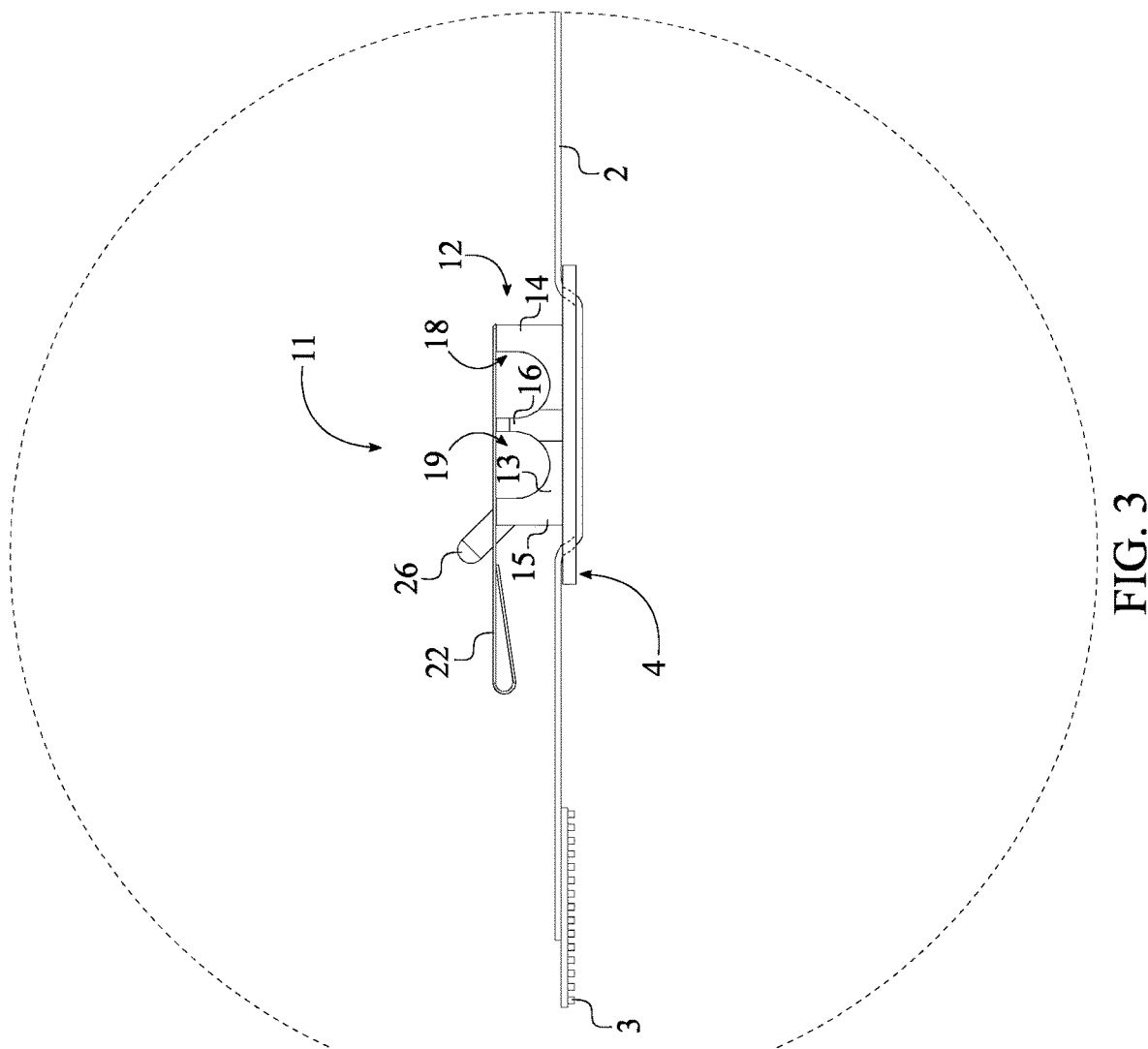
FIG. 3 is a side view of the present invention, wherein the catheter stabilizing retainer is in the closed position.

In reference to the general configuration, the present invention comprises an attachment strap 1, a mounting plate 4, and a catheter stabilizing retainer 11 as shown in FIG. 1-2. The attachment strap 1 that secures the present invention to the patient's leg slidably traverses through the mounting plate 4. The mounting plate 4 functions as a slidable platform so that the catheter stabilizing retainer 11 can be rotatably mounted to the mounting plate 4. The catheter stabilizing retainer 11 that mounts the port divider of the catheter to the present invention comprises a channeled holder 12, an elastic cover 22, and a male fastening feature 26 as shown in FIG. 3. More specifically, a base 13 of the channeled holder 12 is rotatably mounted to the mounting plate 4 thus enabling the port divider of the catheter to move without pulling on the catheter tube. A proximal end 23 of the elastic cover 22 is terminally connected to a first lateral wall 14 of the channeled holder 12. The male fastening feature 26 is angularly connected to a second lateral wall 15 of the channeled holder 12, wherein the male fastening feature 26 and the proximal end 23 of the elastic cover 22 are oppositely positioned of each other about the channeled holder 12. When the port divider is placed within the channeled holder 12, the elastic cover 22 is stretched across the first lateral wall 14 and the second lateral wall 15 of the channeled holder 12 and removably mounted to the male fastening feature 26. As a result, the elastic cover 22 and the channeled holder 12 are able to secure the port divider of the catheter to the present invention.

In reference to FIG. 2-3, the attachment strap 1 comprises an elastic body 2 and a fastening member 3. The elastic body 2, made entirely of stretch material, has a soft and supple backing for added skin comfort. The elasticity and width of the elastic body 2 distribute compression evenly around the thigh to minimize circumferential pressure even if the patient develops edema. The elastic body 2 can be placed anywhere on either of the patients' legs to relieve humidity or moisture against the skin in any particular spot. The fastening member 3 is terminally connected to the elastic body 2, wherein a loop formation of the elastic body 2 allows the fastening member 3 to attach onto the elastic body 2. Preferably, the fastening member 3 is a hook fastening portion from a hook-and-loop fastener. As a result, when the elastic body 2 functions as a loop fastening portion so that the fastening member 3 can adhered onto the elastic body 2 once the attachment strap 1 is looped around the patient's leg. Lastly, the fastening member 3 allows the present invention to be takeoff daily, hourly, or even minute after minute, or reuse, allows for regular and frequent inspection of the skin beneath the attachment strap 1. A minimum width of the elastic body 2 is preferably 2 inches so that the attachment strap 1 does not function as a tourniquet. However, the width of the elastic body 2 can be any width greater than 2 inches. The length of the elastic body 2 ranges from 17 to 25 inches, preferably 19, so that the attachment strap 1 can stretched around different diameter thigh muscles.

Due to the functionality and the placement of the elastic body 2, the present invention is able to prevent or minimize common factors that increase the risk of a medical device related ulcer. More specifically, the elastic body 2 is able to eliminate unnecessary pressure that is created on the patient's skin with the in proper placement or incorrect size of the existing catheter stabilization devices. The present invention also eliminates the friction that can be caused by the device against the skin, particularly in mobile or semi-mobile patients. The present invention also eliminates the humidity and heat that develop between the existing catheter stabilization devices and the patient's skin which can negatively impact the microclimate of the patient's skin and reduce skin's barrier function. The present invention also eliminates risk of an ulcer developing as the elastic body 2 ease the regular inspection of the patient's skin.

Figure 4:
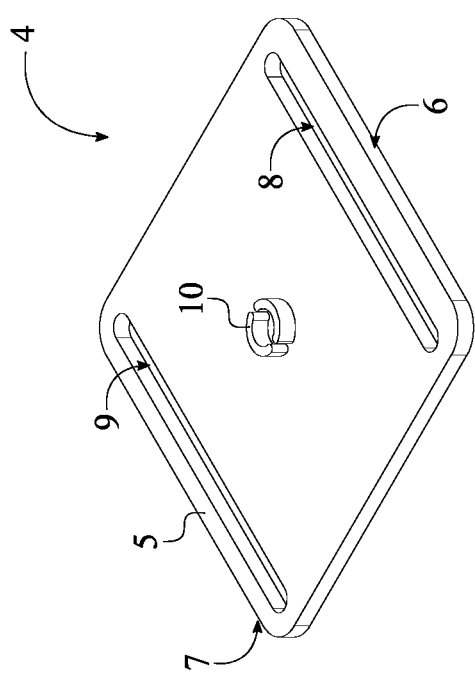
FIG. 4 is a top perspective view of the mounting plate of the present invention.
Figure 5:
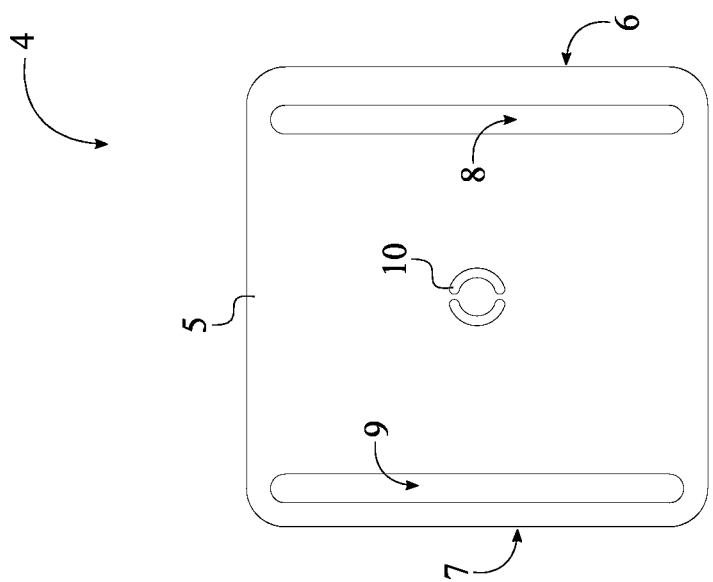
FIG. 5 is a top view of the mounting plate of the present invention.

In reference to FIG. 4-5, the mounting plate 4 comprises a plate body 5, a first elongated opening 8, a second elongated opening 9, and a swivel collar 10. The mounting plate 4 is preferably formed into a rectangular shape without any sharp edges. The first elongated opening 8 and the second elongated opening 9 provide two openings for the plate body 5 so that the elastic body 2 can slidably attach to the mounting plate 4, wherein the first elongated opening 8 and the second elongated opening 9 are positioned parallel to each other. More specifically, the first elongated opening 8 traverses through the plate body 5 and extended along a first edge 6 of the plate body 5. The second elongated opening 9 traverses through the plate body 5 and extended along a second edge 7 of the plate body 5. As a result, the elastic body 2 can be inserted through the first elongated opening 8, extended along a bottom surface of the plate body 5, and inserted through the second elongated opening 9 to slidably attach the mounting plate 4 to the elastic body 2. The swivel collar 10 is concentrically connected onto the plate body 5 thus allowing the catheter stabilizing retainer 11 to rotatably connected to the mounting strap.

Figure 6:
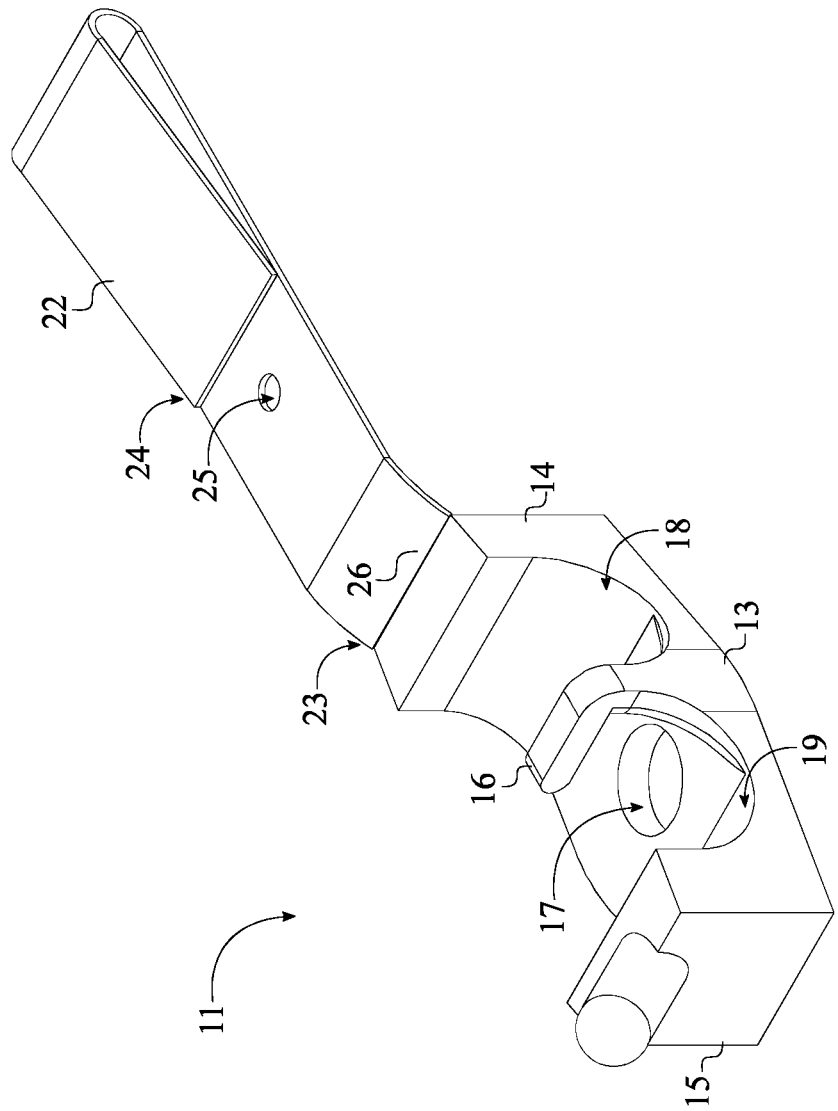
FIG. 6 is a top perspective view of the catheter stabilizing retainer of the present invention.
Figure 7:
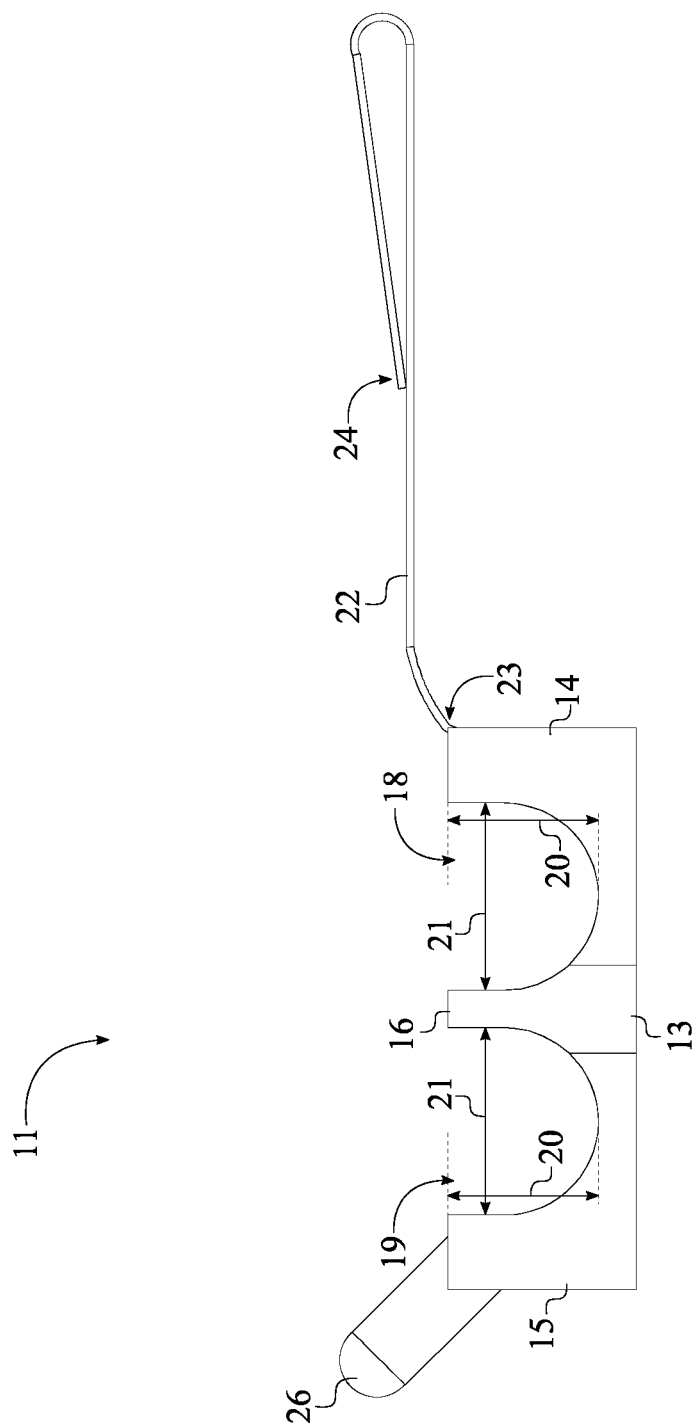
FIG. 7 is a side view of the catheter stabilizing retainer of the present invention.

In reference to FIG. 6-7, the channeled holder 12 further comprising a hook section 16, a first channel 18, and a second channel 19. More specifically, the first lateral wall 14 is terminally connected to the base 13. The second lateral wall 15 is terminally connected to the base 13 and positioned opposite of the first lateral wall 14. The first lateral wall 14 and the second lateral wall 15 function as channel walls so that the port divider can be held within the catheter stabilizing retainer 11. The hook section 16 is positioned in between the first lateral wall 14 and the second lateral wall 15 and terminally connected onto the base 13. The hook section 16 functions as an inverted hook to prevent slippage of the port divider within the catheter stabilizing retainer 11. The first channel 18 and the second channel 19 allow the ambidextral placement of the port divider within the catheter stabilizing retainer 11. The first channel 18 is delineated by the first lateral wall 14, the base 13, and the hook section 16. The second channel 19 is delineated by the second lateral wall 15, the base 13, and the hook section 16. furthermore, a depth 20 of the first channel 18 is equal to a depth 20 of the second channel 19, and a width 21 of the first channel 18 is equal to a width 21 of the second channel 19. Due to the identical sizes of the first channel 18 and the second channel 19, a drainage port and a balloon port of the port divider can be ambidextraly placed with the catheter stabilizing retainer 11. For example, in some embodiment of the present invention, the drainage port can be placed within the first channel 18 and the balloon port can be placed within the second channel 19. In some embodiment of the present invention, the drainage port can be placed within the second channel 19 and the balloon port can be placed within the first channel 18.

Figure 9:
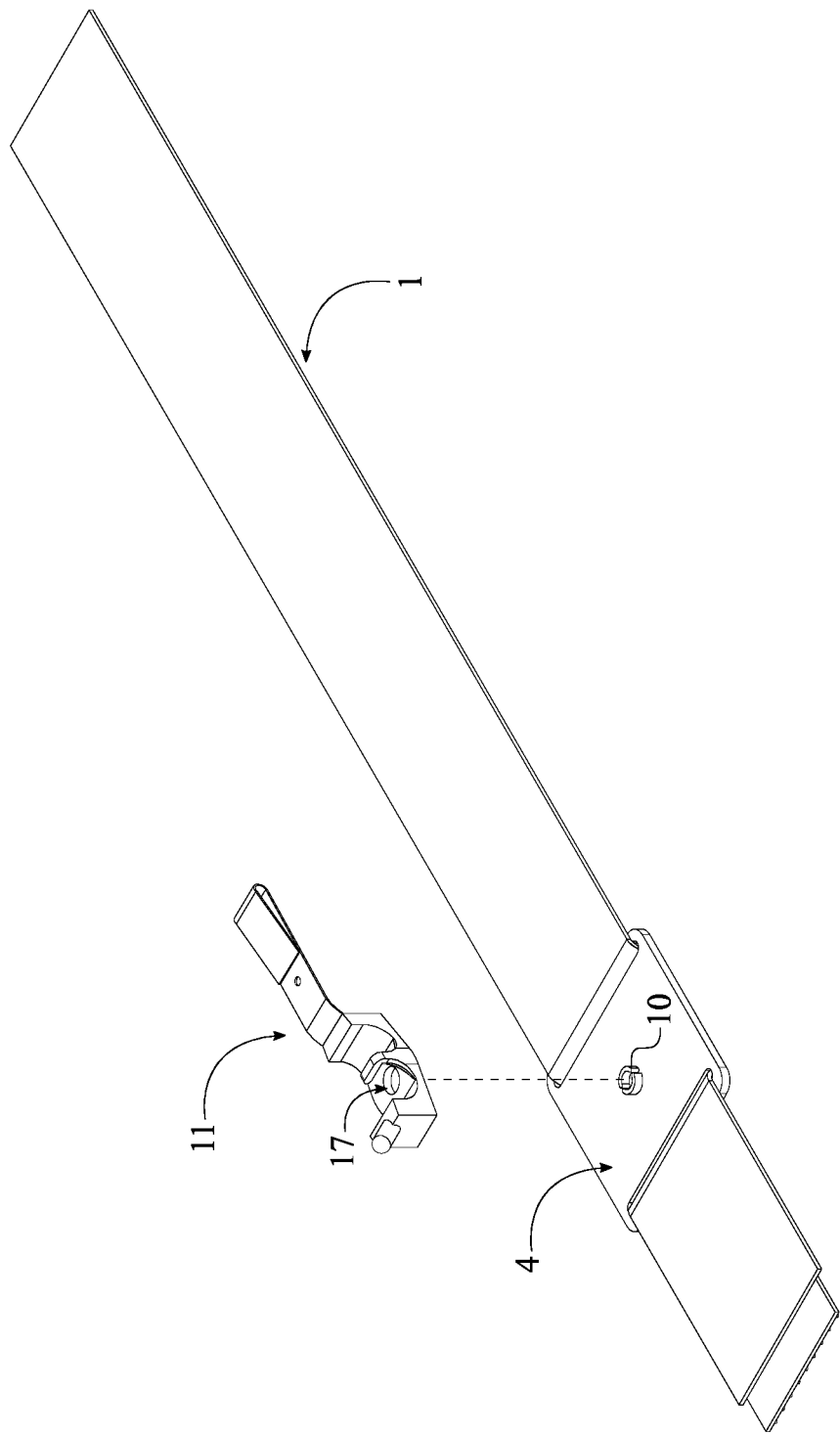
FIG. 9 is an exploded perspective view of the present invention, wherein the catheter stabilizing retainer is in the opened position.

In reference to FIG. 9, the channeled holder 12 further comprises a swivel opening 17. More specifically, the swivel opening 17 concentrically traversing through the base 13 so that the swivel opening 17 can be rotatably engaged to the swivel collar 10. Due to the rotatable connection between the swivel opening 17 and the swivel collar 10, the channeled holder 12 is able to rotate about the plate body 5. As a result, the catheter stabilizing retainer 11 allows the port divider of the catheter to rotatably move without pulling on the catheter tube or the elastic body 2.

In reference to FIG. 6-7, the elastic cover 22 comprises a distal end 24 and a female fastening feature 25 in addition to the proximal end 23. The elastic cover 22, made entirely of stretch material, is designed to securely lock in the port divider within the channeled holder 12. More specifically, the distal end 24 is formed into a loop section so that the patient can easily place their finger or an external device into the loop section for ease of operation. The female fastening feature 25 is integrated into the elastic cover 22 and positioned in between the loop section and the proximal end 23. Preferably, the female fastening feature 25 is a reinforced opening within the elastic cover 22 so that the female fastening feature 25 can be selectively engaged with the male fastening feature 26. Due to the simplistic configuration of the elastic cover 22, the present invention can be easily operated by a patient with hand dexterity and limited mobility issues. Furthermore, the angular positioning of the male fastening feature 26 and the elasticity of the elastic cover 22 prevent accidental or unintentional disengagement of the elastic cover 22.

Figure 8:
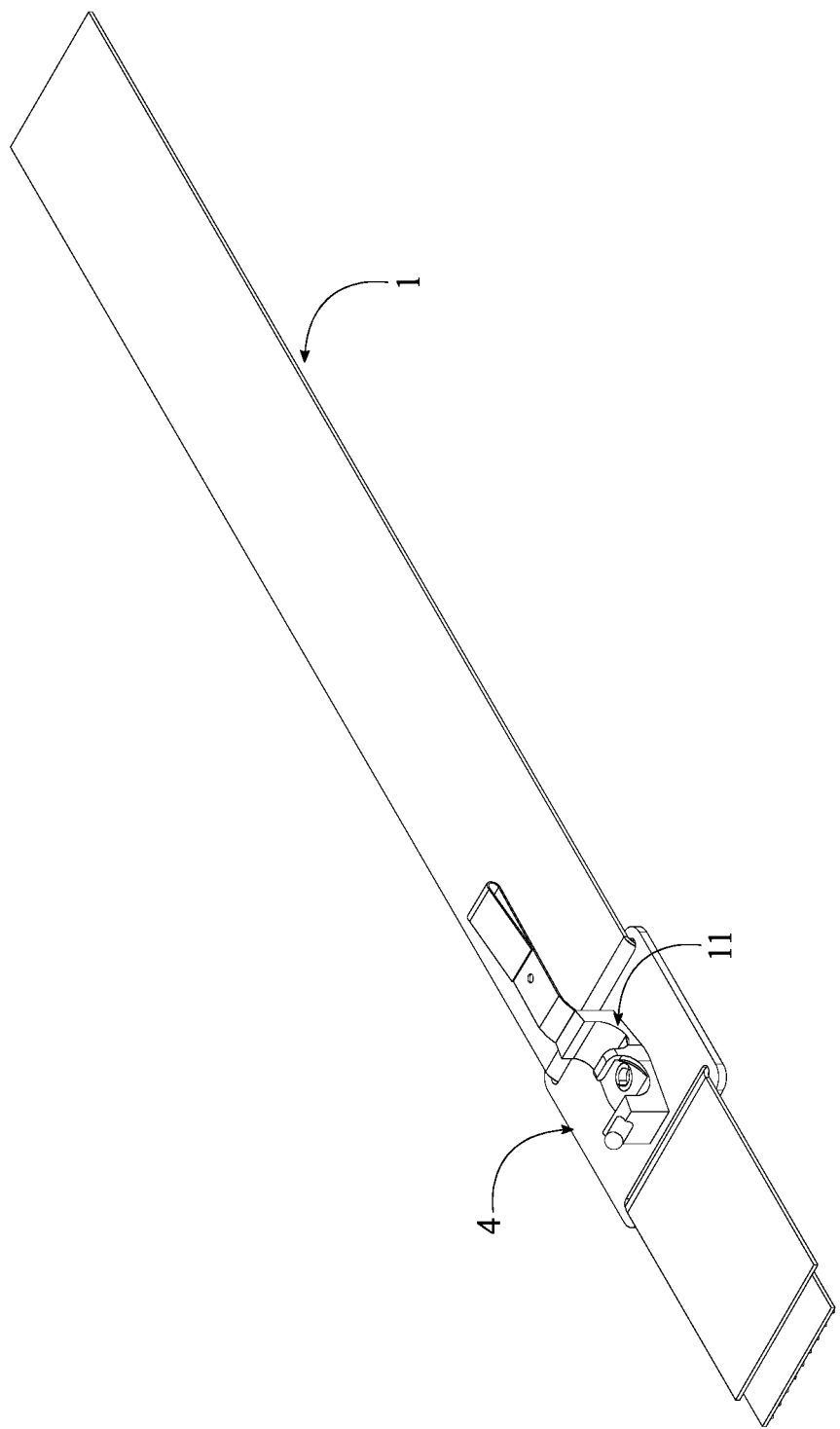
FIG. 8 is a top perspective view of the present invention, wherein the catheter stabilizing retainer is in the opened position.

In reference to FIG. 1, when the distal end 24 of the elastic cover 22 is stretched across the first lateral wall 14 and the second lateral wall 15 and removably mounted to the male fastening feature 26, the present invention is configured as a closed position as the port divider is secured within the first channel 18 and the second channel 19. In reference to FIG. 8, when the distal end 24 of the elastic cover 22 is positioned away from the first lateral wall 14 and the second lateral wall 15 and disengaged from the male fastening feature 26, the present invention is configured as an opened position as the port divider can be removed or placed within the first channel 18 and the second channel 19.

Although the invention has been explained in relation to its preferred embodiment, it is to be understood that many other possible modifications and variations can be made without departing from the spirit and scope of the invention as hereinafter claimed.

What is claimed is:
1. A foley catheter stabilizing apparatus comprising:
an attachment strap;
a mounting plate;
a catheter stabilizing retainer;

the catheter stabilizing retainer comprising a channeled holder, an elastic cover, and a male fastening feature;

the attachment strap slidably traversing through the mounting plate;

a base of the channeled holder being rotatably mounted to the mounting plate;

a proximal end of the elastic cover being terminally connected to a first lateral wall of the channeled holder;

the male fastening feature being angularly connected to a second lateral wall of the channeled holder;

the male fastening feature and the proximal end of the elastic cover being oppositely positioned of each other about the channeled holder;

the elastic cover being stretched across the first lateral wall and the second lateral wall of the channeled holder;

the elastic cover being removably mounted to the male fastening feature;

the channeled holder further comprising a hook section;

the first lateral wall being terminally connected to the base;

the second lateral wall being terminally connected to the base, opposite of the first lateral wall;

the hook section being positioned in between the first lateral wall and the second lateral wall;

the hook section being terminally connected onto the base.

2. The foley catheter stabilizing apparatus as claimed in claim 1 comprising:

the attachment strap comprising an elastic body and a fastening member; and the fastening member being terminally connected to the elastic body, wherein a loop formation of the elastic body allows the fastening member to attach onto the elastic body.

3. The foley catheter stabilizing apparatus as claimed in claim 2, wherein a minimum width of the elastic body is 2 inches.

4. The foley catheter stabilizing apparatus as claimed in claim 1 comprising:

the mounting plate comprising a plate body, a first elongated opening, a second elongated opening, and a swivel collar;

the first elongated opening and the second elongated opening being positioned parallel to each other;

the first elongated opening traversing through the plate body;

the first elongated opening being extended along a first edge of the plate body;

the second elongated opening traversing through the plate body;

the second elongated opening being extended along a second edge of the plate body; and the swivel collar being concentrically connected onto the plate body.

5. The foley catheter stabilizing apparatus as claimed in claim 1 comprising:

the channeled holder further comprising a first channel and a second channel;

the first channel being delineated by the first lateral wall, the base, and the hook section;

the second channel being delineated by the second lateral wall, the base, and the hook section;

a depth of the first channel being equal to a depth of the second channel; and a width of the first channel being equal to a width of the second channel.

6. The foley catheter stabilizing apparatus as claimed in claim 1 comprising:

the channeled holder further comprising a swivel opening;

the mounting plate comprising a swivel collar;

the swivel opening concentrically traversing through the base; and the swivel opening being rotatably engaged to the swivel collar.

7. The foley catheter stabilizing apparatus as claimed in claim 1 comprising:

the elastic cover comprising a distal end and a female fastening feature;

the distal end being formed into a loop section;

the female fastening feature being integrated into the elastic cover;

the female fastening feature being positioned in between the loop section and the proximal end; and the female fastening feature being selectively engaged with the male fastening feature.

* * * * *